US011883411B2

(12) United States Patent
Zhang et al.

(10) Patent No.: US 11,883,411 B2
(45) Date of Patent: Jan. 30, 2024

(54) USE OF COMPOUND APREPITANT IN PREPARATION OF DRUG FOR PREVENTING OR TREATING AFRICAN SWINE FEVER (ASF)

(71) Applicant: LANZHOU VETERINARY RESEARCH INSTITUTE, CHINESE ACADEMY OF AGRICULTURAL SCIENCES, Lanzhou (CN)

(72) Inventors: Keshan Zhang, Lanzhou (CN); Haixue Zheng, Lanzhou (CN); Huimei Cui, Lanzhou (CN); Bo Yang, Lanzhou (CN); Hong Tian, Lanzhou (CN); Zixiang Zhu, Lanzhou (CN); Tao Feng, Lanzhou (CN); Fan Yang, Lanzhou (CN); Weijun Cao, Lanzhou (CN); Xusheng Ma, Lanzhou (CN); Yi Ru, Lanzhou (CN); Jianhong Guo, Lanzhou (CN); Xiangtao Liu, Lanzhou (CN)

(73) Assignee: LANZHOU VETERINARY RESEARCH INSTITUTE, CHINESE ACADEMY OF AGRICULTURAL SCIENCES, Lanzhou (CN)

( * ) Notice: Subject to any disclaimer, the term of this patent is extended or adjusted under 35 U.S.C. 154(b) by 0 days.

(21) Appl. No.: 17/895,390

(22) Filed: Aug. 25, 2022

(65) Prior Publication Data
US 2023/0270747 A1  Aug. 31, 2023

Related U.S. Application Data

(63) Continuation of application No. PCT/CN2022/098311, filed on Jun. 13, 2022.

(30) Foreign Application Priority Data

Feb. 25, 2022  (CN) .......................... 202210181584.1

(51) Int. Cl.
*A61K 31/5377* (2006.01)
*A61P 31/20* (2006.01)

(52) U.S. Cl.
CPC .......... *A61K 31/5377* (2013.01); *A61P 31/20* (2018.01)

(58) Field of Classification Search
CPC ........................... A61K 31/5377; A61P 31/20
See application file for complete search history.

(56) References Cited

U.S. PATENT DOCUMENTS

| 2009/0209541 A1 | 8/2009 | Jain et al. |
| 2010/0009970 A1 | 1/2010 | Johansen et al. |
| 2017/0290774 A1 | 10/2017 | Ruiz et al. |

FOREIGN PATENT DOCUMENTS

| CN | 111588721 A | 8/2020 |
| KR | 2254246 B1 * | 5/2021 |

(Continued)

OTHER PUBLICATIONS

Xu et al. "Substance P and its role in viral infection," In.J. Clin. Exp. Med. 2018, 11(12) 12946-12955 (Year: 2018).*

(Continued)

*Primary Examiner* — Shengjun Wang
(74) *Attorney, Agent, or Firm* — MH2 TECHNOLOGY LAW GROUP LLP

(57) ABSTRACT

The present disclosure belongs to the technical field of African swine fever (ASF) treatment, in particular to use of a compound aprepitant in prevention or treatment of the ASF. In the present disclosure, it is found that the compound aprepitant can significantly inhibit replication of an African swine fever virus (ASFV); in addition, it is found that the aprepitant inhibits transcription and protein expression of D1133L, and reduces transcription and protein expression levels of p30 and p72, preventing virus invasion on host cells. Therefore, the compound aprepitant can be used to (Continued)

inhibit early and late infection of the ASFV. Accordingly, the compound aprepitant can be used to prevent or treat the ASF.

4 Claims, 8 Drawing Sheets

Specification includes a Sequence Listing.

(56) References Cited

FOREIGN PATENT DOCUMENTS

| WO | WO-2014179751 A1 * | 11/2014 | ........... A61K 31/713 |
|----|---|---|---|
| WO | 2020225283 A1 | 11/2020 | |
| WO | 2021191108 A1 | 9/2021 | |

OTHER PUBLICATIONS

Van Gorp et al. "Scavenger receptor CD 163, a jack-of-all-trades and potential target for cell-directed therapy," Molecular Immunology, 2010, vol. 47, pp. 1650-1660 (Year: 2010).*
Chinese First Office Action dated Aug. 29, 2022 in corresponding Chinese Application No. 202210181584.1, translated, 10 pages.

* cited by examiner

USE OF COMPOUND APREPITANT IN PREPARATION OF DRUG FOR PREVENTING OR TREATING AFRICAN SWINE FEVER (ASF)

CROSS REFERENCE TO RELATED APPLICATION

The present application is a continuation of International Application No. PCT/CN2022/098311 filed on Jun. 13, 2022, which claims the priority to Chinese Patent Application No. 202210181584.1, titled "USE OF COMPOUND APREPITANT IN PREPARATION OF DRUG FOR PREVENTING OR TREATING AFRICAN SWINE FEVER (ASF)" filed Feb. 25, 2022, which is incorporated herein by reference in its entirety.

SEQUENCE LISTING

The instant application contains a Sequence Listing XML which has been submitted electronically in XML format and is hereby incorporated by reference in its entirety. Said XML copy, created on Aug. 16, 2022, is named 2022-08-25_HLPCTP20220501018.xml and is 11 kilobytes in size.

TECHNICAL FIELD

The present disclosure belongs to the technical field of African swine fever (ASF) treatment, in particular to use of a compound aprepitant in preparation of a drug for prevention or treatment of the ASF.

BACKGROUND ART

African swine fever (ASF) is an acute and highly-contagious disease caused by African swine fever virus (ASFV) infection, with a mortality rate as high as 100%. Since the introduction into China in 2018, the ASF has caused significant economic losses to the domestic pig industry. There is currently no commercial vaccine, such that the development of effective antiviral drugs at a reasonable cost is of great significance for the treatment of ASF. Although various types of active anti-ASFV drugs have been reported, an in vivo efficacy of these compounds has not been evaluated.

ASFV is a double-stranded DNA virus that replicates primarily in monocytes and macrophages, encoding more than 50 structural proteins and 100 nonstructural proteins.

Aprepitant, also known as Emend, has a molecular formula of $C_{23}H_{21}F_7N_4O_3$, a CAS number of 170729-80-3, and a chemical name of 5-[2(R)-[1(R)-[3,5-bis(trifluoromethyl)phenyl]ethoxy]-3(S)-(4-fluorophenyl)morpholino-4-ylmethyl]-3,4-dihydro-2H-1,2,4-triazol-3-one. A structural formula is:

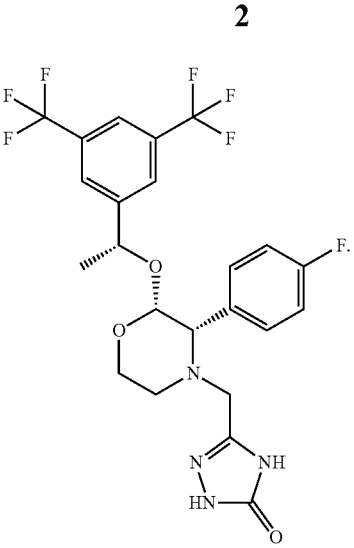

Aprepitant was approved by the Food and Drug Administration (FDA) in 2003 for treating chemotherapy-induced vomiting, and was the first NK-1 receptor antagonist to be marketed; meanwhile, the aprepitant achieves a specific anti-tumor effect through the NK-1 receptor, and can be used as a broad-spectrum anti-tumor drug. In addition, the aprepitant also exhibits an anti-HIV-1 activity. The compound has been reported in academic articles by researchers such as Muñoz Miguel and Manak Mark M (referring to Muñoz Miguel, Rosso Marisa. The NK-1 receptor antagonist aprepitant as a broad spectrum antitumor drug. [J]. *Invest New Drugs*, 2010, 28:187-93.;Manak Mark M, Moshkoff Dmitry A, Nguyen Lequan T et al. Anti-HIV-1 activity of the neurokinin-1 receptor antagonist aprepitant and synergistic interactions with other antiretrovirals. [J]. *AIDS*, 2010, 24:2789-96.). However, no studies have shown that the aprepitant has an anti-ASFV effect.

SUMMARY

In the present disclosure, it is found that the compound aprepitant can significantly inhibit replication of the ASFV. In addition, it is found that the aprepitant inhibits transcription and protein expression of D1133L, and reduces transcription and protein expression levels of p30 and p72, preventing virus invasion on host cells. Therefore, the compound aprepitant can be used to inhibit early and late infection of the ASFV. Accordingly, the compound aprepitant can be used to prevent or treat the ASF. Accordingly, the compound aprepitant can be used to prevent or treat the ASF.

The compound aprepitant has a molecular formula of $C_{23}H_{21}F_7N_4O_3$, a CAS number of 170729-80-3, and a chemical name of 5-[2(R)-[1(R)-[3,5-bis(trifluoromethyl)phenyl]ethoxy]-3(S)-(4-fluorophenyl)morpholino-4-ylmethyl]-3,4-dihydro-2H-1,2,4-triazol-3-one; and a structural formula is shown in formula (I):

(I)

The present disclosure provides use of a compound aprepitant in preparation of a drug for treating ASF.

The present disclosure further provides use of a compound aprepitant in preparation of a drug for preventing ASF.

The present disclosure further provides use of a compound aprepitant in preparation of a drug for inhibiting gene transcription of an ASFV. The gene of the ASFV is one or more genes selected from the group consisting of a D1133L gene, a p30 gene, and a p72 gene of the ASFV.

The present disclosure further provides use of a compound aprepitant in preparation of a drug for inhibiting protein expression of an ASFV. The protein of the ASFV is one or more selected from the group consisting of a D1133L protein, a p30 protein, and a p72 protein of the ASFV.

Preferably, the drug may be obtained by adding a pharmaceutically acceptable carrier and/or auxiliary material to the compound aprepitant to prepare any dosage form of a tablet, a spray, a granule, a capsule, an oral solution, an injection, or a suspension.

The present disclosure has the following beneficial effects:

In the present disclosure, it is found that the compound aprepitant can significantly inhibit replication of an ASFV; in addition, it is found that the aprepitant inhibits transcription and protein expression ofD1133L, and reduces transcription and protein expression levels ofp30 and p72, preventing virus invasion on host cells. Therefore, the compound aprepitant can be used to inhibit early and late infection of the ASFV. Accordingly, the compound aprepitant can be used to prevent or treat the ASF.

BRIEF DESCRIPTION OF THE DRAWINGS

FIG. 1A shows an effect of DMSO on virus infection and replication after treatment of cells, and FIG. 1B shows an effect of aprepitant on virus infection and replication after treatment of cells; GFP and TRANS rows indicate observation under green fluorescence and white light, respectively; and ASFV and DMSO columns, 18 μM, 22 μM, and 24 μM represent cells treated with ASFV fluorescent virus, ASFV fluorescent virus +DMSO, and ASFV fluorescent virus mixed with different concentrations of aprepitant (18 μM, 22 μM, and 24 μM) diluted by DMSO;

FIG. 2A shows an inhibitory effect of the DMSO on virus replication, and FIG. 2B shows a comparison of the inhibitory effect of different concentrations of compound aprepitant on ASFV replication;

FIG. 5A shows inhibition of the p30 transcription of ASFV by the compound aprepitant, and FIG. 5B shows inhibition of the p72 transcription of ASFV by the compound aprepitant;

FIG. 7A is a result of p30 protein expression level, and FIG. 7B is a result of p72 protein expression level.

DESCRIPTION OF THE BIOLOGICAL PRESERVATION

Figure 1A:
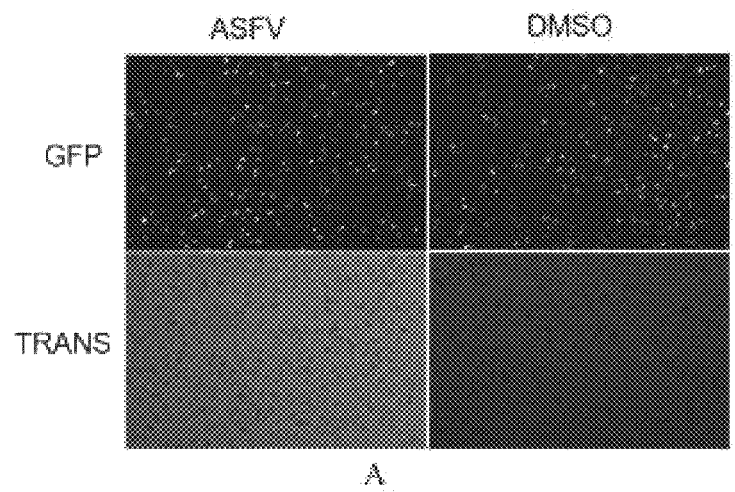
FIG. 1A-1B shows a fluorescence image of a compound aprepitant inhibiting ASFV; where

Date of deposit: Monday, Dec. 21, 2020;
Institution of deposit: China Center for Type Culture Collection (CCTCC);
Deposit number: CCTCC NO: V202096;
Address: Wuhan University, China;
Classification name: Type II African swine fever virus strain ASFV CN/GS 2018.

DETAILED DESCRIPTION OF THE EMBODIMENTS

The present disclosure is further described below with reference to the accompanying drawings and examples.

The relevant experiments described in the following examples have obtained a biosafety license and a ASF laboratory activity license:

According to the relevant requirements of biosafety level 3 (BSL-3) laboratory and FMD-related biosafety, the Lanzhou Veterinary Research Institute of the Chinese Academy of Agricultural Sciences has reported to the Biosafety Committee of the Lanzhou Veterinary Research Institute, the Ethics Committee on Laboratory Animals, the Biosafety Commission of the Chinese Academy of Agricultural Sciences, the Laboratory Animal Ethics Committee of the Lanzhou Veterinary Research Institute, and the Biosafety Committee of the Lanzhou Veterinary Research Institute. The Lanzhou Veterinary Research Institute of the Chinese Academy of Agricultural Sciences has obtained a permission of the Ministry of Agriculture to conduct research on highly-pathogenic ASFV pathogens and animals, and has been filed with the Ministry of Agriculture and Rural Affairs, thereby meeting the requirements of the national biosafety level.

The experimental cells and virus sources described in the examples are as follows:

Primary porcine alveolar macrophages (PAMs) and primary bone marrow-derived macrophage (BMDMs) were collected from piglets about 5 weeks old; the cells were aseptically collected, red blood cells were removed with a red blood cell lysate (purchased from Biosharp), and a supernatant was discarded after low-speed centrifugation; a cell pellet was resuspended in an RPMI 1640 complete medium (purchased from Gibco) containing 10% FBS (purchased from Gibco), and then cultured in a 37° C., 5% $CO_2$ incubator.

ASFV was a strain CN/GS 2018; an ASFV CN/GS 2018 isolate came from the National African Swine Fever Regional Laboratory (Lanzhou), belonged to genotype II, and had a virus titer of $5 \times 10^7$ $TCID_{50}$/mL, which was a fourth-generation virus after PAM cell expansion; the strain was deposited in the CCTCC on Dec. 21, 2020, with a deposit number of CCTCC NO: V202096. ASFV fluorescent virus was an ASFV fluorescent virus containing an eGFP selection expression cassette gene fragment and an MGF-360-9L gene deleted. A preparation method of the virus referred to Chinese patent CN111593028A.

A compound aprepitant was purchased from Topscience Co., Ltd. (Shanghai).

In the examples, other reagents were common commercially-available reagents unless otherwise specified; and operations were known in the art unless otherwise specified.

EXAMPLE 1

Effects of a compound aprepitant on ASFV replication and gene transcription and expression 1. Observation of an effect of the compound aprepitant on ASFV infection and replication under fluorescence Porcine alveolar macrophages (PAM, $1 \times 10^6$/well) were cultured with an RPMI 1640+10% FBS medium in a 12-well plate, where in an experimental group, cells were treated with ASFV fluorescent virus (MOI=0.1) mixed with different concentrations of aprepitant (18 μM, 22 μM, 24 μM) dissolved in DMSO (<1%); in the infection control group, cells were treated with ASFV fluorescent virus (MOI=0.1) mixed with DMSO (<1%). In addition, cells treated with only ASFV fluorescent virus (MOI=0.1) were used as an infection blank group. The cell plate was cultured at 37° C. in 5% $CO_2$ for 48 h, and fluorescence changes were observed under a microscope.

The result is shown in FIG. 1. FIG. 1A shows that under fluorescence and white light, there is no significant difference between the infection control group and the infection blank group, indicating that DMSO has no effect on virus infection and replication.

Figure 1B:
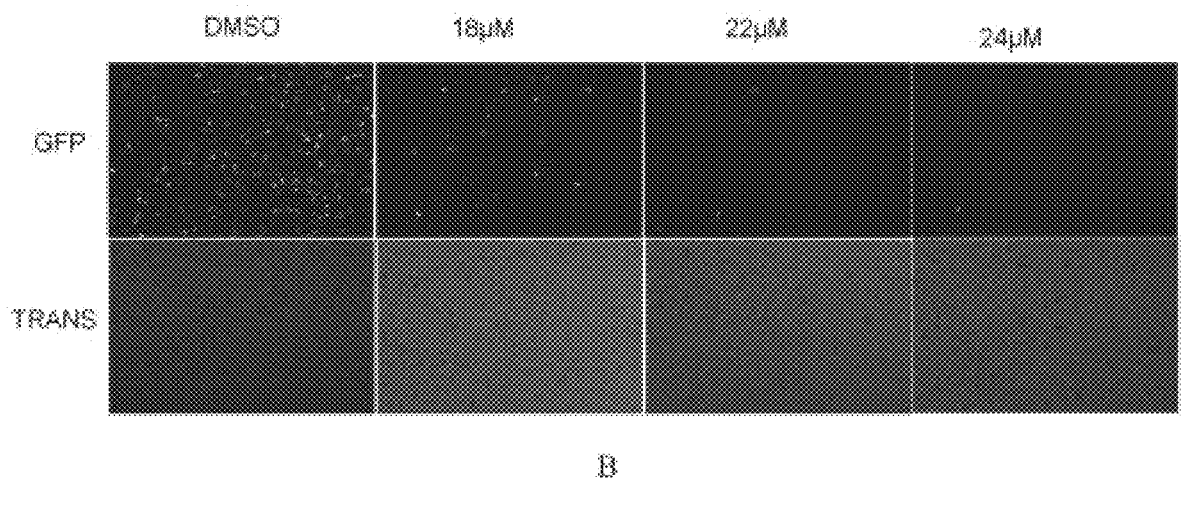

FIG. 1B shows that the fluorescence is brighter in the infection control group (DMSO), while the fluorescence gradually becomes darker after treatment with different concentrations of aprepitant; the fluorescence completely disappears when being treated with 24 μM aprepitant. The above results show that the compound aprepitant can significantly inhibit the infection and replication of ASFV, and has a more obvious inhibitory effect with the increase of the compound concentration.

2. Effects of the compound aprepitant on the copy number of a viral genome during ASFV infection and replication Porcine alveolar macrophages (PAM, $1 \times 10^6$/well) were cultured with an RPMI 1640+10% FBS medium in a 12-well plate, where in an experimental group, cells were treated with ASFV fluorescent virus (MOI=0.1) mixed with different concentrations of aprepitant (18 μM, 20 μM, 22 μM) dissolved in DMSO (<1%); in the infection control group, cells were treated with ASFV fluorescent virus (MOI=0.1) mixed with DMSO (<1%). In addition, cells treated with only ASFV fluorescent virus (MOI=0.1) were used as an infection blank group. The cell plate was cultured at 37° C. with 5% $CO_2$ for 48 h, and then placed at −80° C. for three times of inactivation by freezing and thawing, and the copy number of the viral genome was detected by RT-qPCR. An RT-qPCR reaction system had a total volume of 20 μL, including: 10 μL of a Premix Ex Taq (2×), 0.2 μL of a ROX Reference Dye II (50×), 0.6 μL of a primer, 0.1 μL of an ASFV probe primer, 2 μL of a template, supplemented with sterile deionized water to 20 μL. The reaction was conducted by: at 50° C. for 2 min; at 95° C. for 2 min; at 95° C. for 15 sec; at 58° C. for 1 min; conducting 45 cycles in total.

ASFV-p72 upstream primer: 5'-GATACCACAA-GATCAGCCGT-3' (SEQ ID NO: 1); downstream primer: 5'-CTGCTCATGGTATCAATCTTATCGA-3' (SEQ ID NO: 2); ASFV probe primer: 5'-CCACGGGAGGAATACCAA CCCAGTG-3' (SEQ ID NO: 3).

Figure 2B:
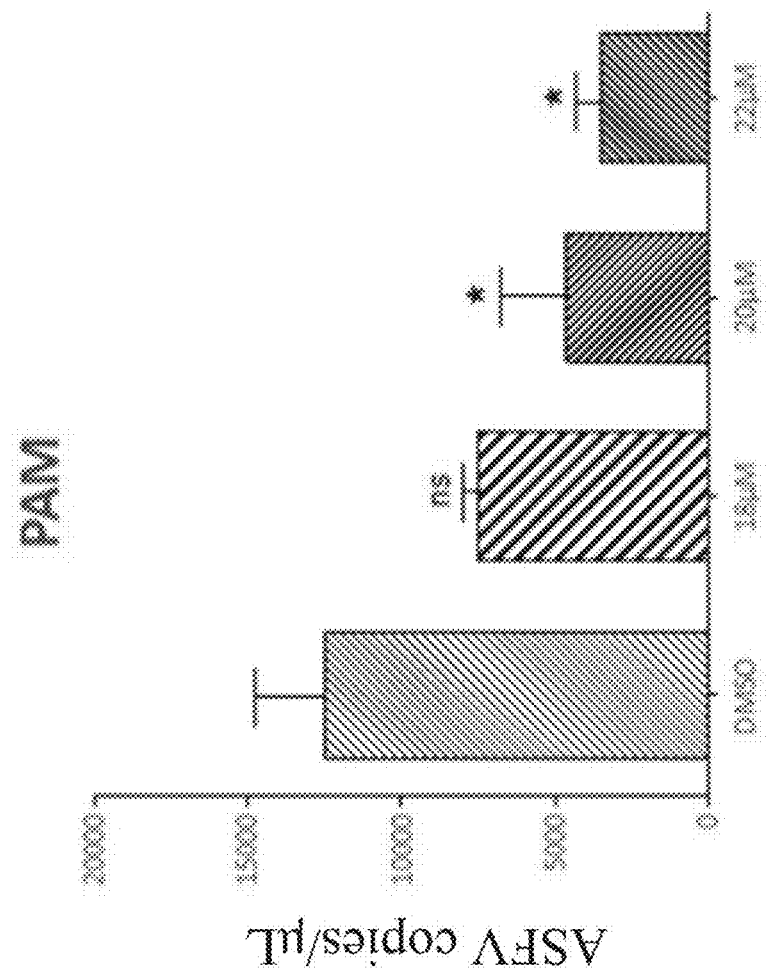
FIG. 2A-2B shows results of the compound aprepitant inhibiting the copy number of an ASFV genome; where
Figure 2A:
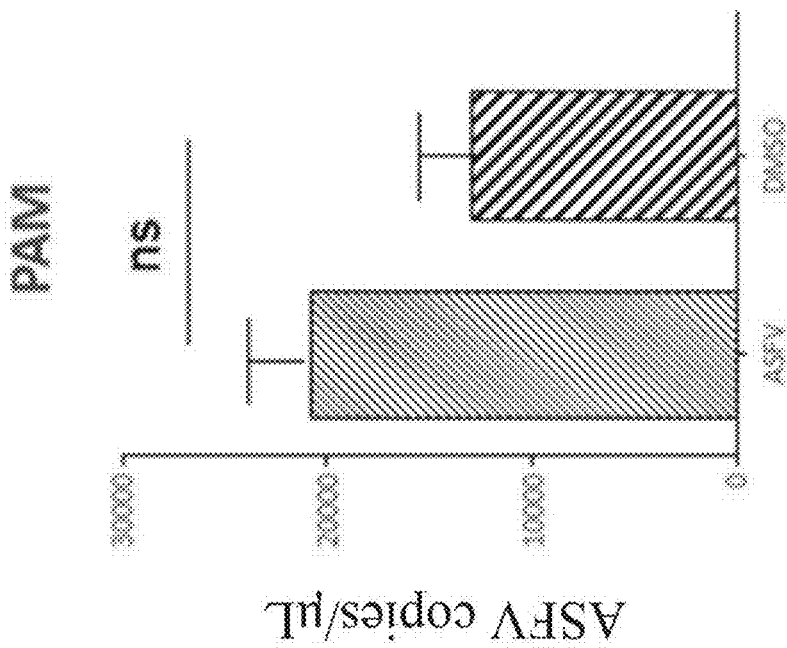

The detection results of ASFV genome copy number are shown in FIG. 2. FIG. 2A shows a comparison of virus replication between the infection control group and the infection blank group, indicating that the inhibitory effect of DMSO on virus replication is not significantly different from that of the blank group.

FIG. 2B shows a comparison of the inhibitory effect of different concentrations of compound aprepitant on ASFV replication; the figure shows that the ASFV genome copy number is reduced after adding the compound aprepitant, and the compound aprepitant at a dosage of 22 μM inhibits the ASFV genome copy number by more than 50%.

3. Effects of the compound aprepitant on the $TCID_{50}$ of ASFV

Porcine bone marrow-derived macrophages (BMDM, $1 \times 10^6$/well) were cultured with an RPMI 1640+10% FBS medium in a 12-well plate, where in an experimental group, cells were treated with ASFV fluorescent virus (MOI=0.1) mixed with different concentrations of aprepitant (22 μM and 44 μM) dissolved in DMSO (<1%); in the infection control group, cells were treated with ASFV fluorescent virus (MOI=0.1) mixed with DMSO (<1%). The cell plate was cultured at 37° C. with 5% $CO_2$ for 48 h, and then frozen and thawed at −80° C. for three times as samples; the samples were serially diluted 10-fold with a serum-free RPMI 1640 to obtain 6 dilutions, and each dilution was repeated in 8 wells, and inoculated into BMDMs for culture; the cell plate was cultured at 37° C. under 5% $CO_2$ for 5 d, and fluorescence changes in each cell culture well were observed every day, and the $TCID_{50}$ was calculated.

Figure 3:
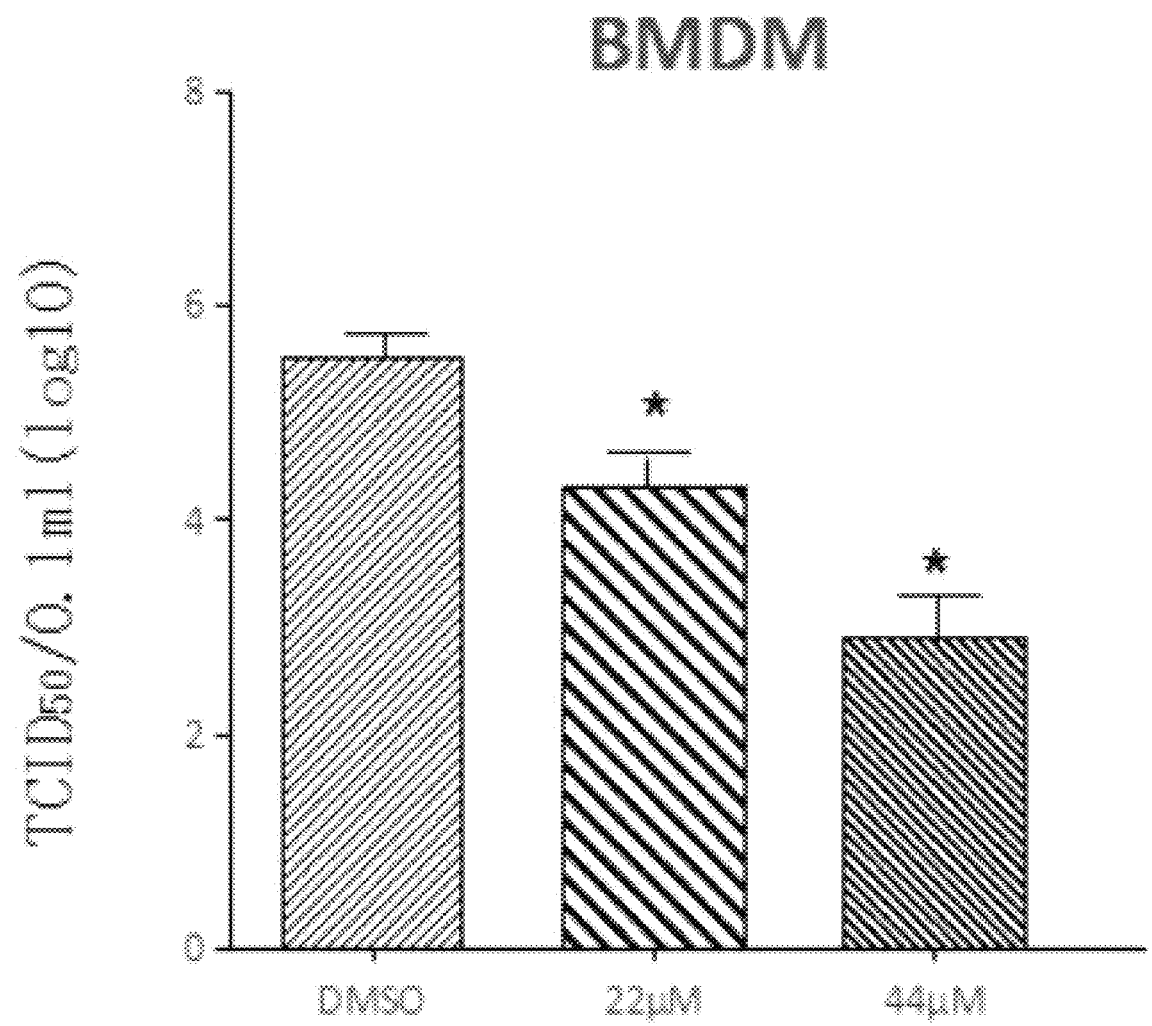
FIG. 3 shows $TCID_{50}$ results of the compound aprepitant inhibiting the ASFV.

The results are shown in FIG. 3, 22 μM and 44 μM compound aprepitant each can reduce the $TCID_{50}$ of ASFV fluorescent virus; when the compound aprepitant has a concentration of 44 μM, the ASFV fluorescent virus has the minimum TCIDso.

4. Effects of the compound aprepitant on D1133L RNA transcript level of ASFV

Porcine alveolar macrophages (PAM, $1 \times 10^6$/well) were cultured with an RPMI 1640+10% FBS medium in a 12-well plate, where in an experimental group, cells were treated with ASFV fluorescent virus (MOI=0.1) mixed with different concentrations of aprepitant (22 μM and 44 μM) dissolved in DMSO (<1%); in the infection control group, cells were treated with ASFV fluorescent virus (MOI=0.1) mixed with DMSO (<1%). The cell plate was cultured at 37° C. in 5% $CO_2$ for 48 h, and a cell culture was collected and centrifuged, and a supernatant was discarded. A total RNA was extracted by a TrizoL method, cDNA was synthesized by an RT Primer Mix kit, and the expression difference of the D1133L RNA was detected by an RT-qPCR method.

An RT-qPCR reaction system had a total volume of 10 μL, including: 0.4 μL of each of upstream and downstream primers, 2 μL of the cDNA, 5 μL of TB Green™ Premix Ex Taq (TaKaRa), supplemented with sterile deionized water to 10 μL. The reaction was conducted by: at 95° C. for 2 min; at 95° C. for 10 sec; at 60° C. for 34 sec; conducting 40 cycles in total.

The primer sequences for amplifying D1133L were: upstream primer: 5'-CTTCTGGAAAACGGGGTACA-3' (SEQ ID NO: 4); downstream primer: 5'-CAAGA-TAAGAACCCCCGACA-3' (SEQ ID NO: 5).

Figure 4:
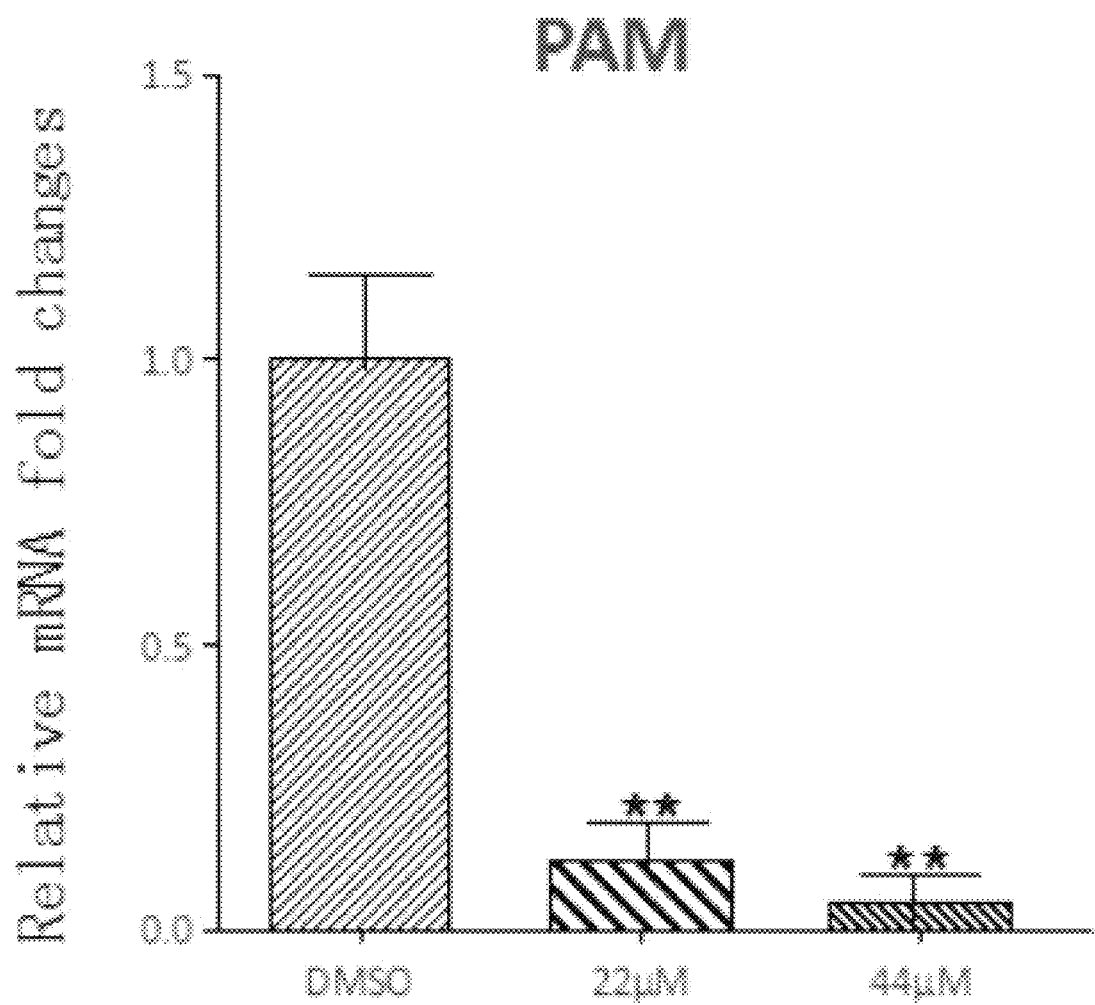
FIG. 4 shows that the compound aprepitant inhibits D1133L transcription of the ASFV.
Figure 5A:
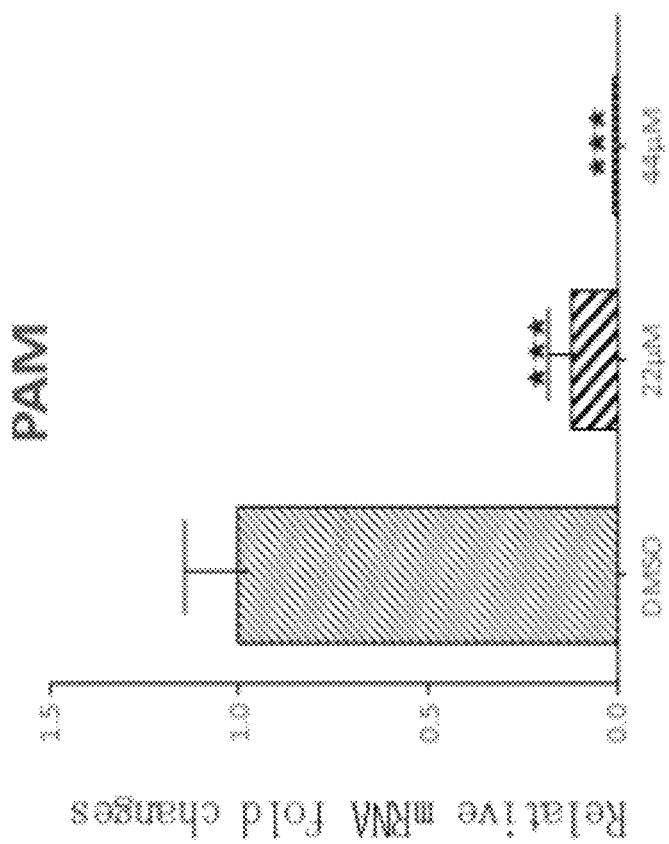
FIG. 5A-5B shows that the compound aprepitant inhibits p30 and p72 transcription of the ASFV; where
Figure 5B:
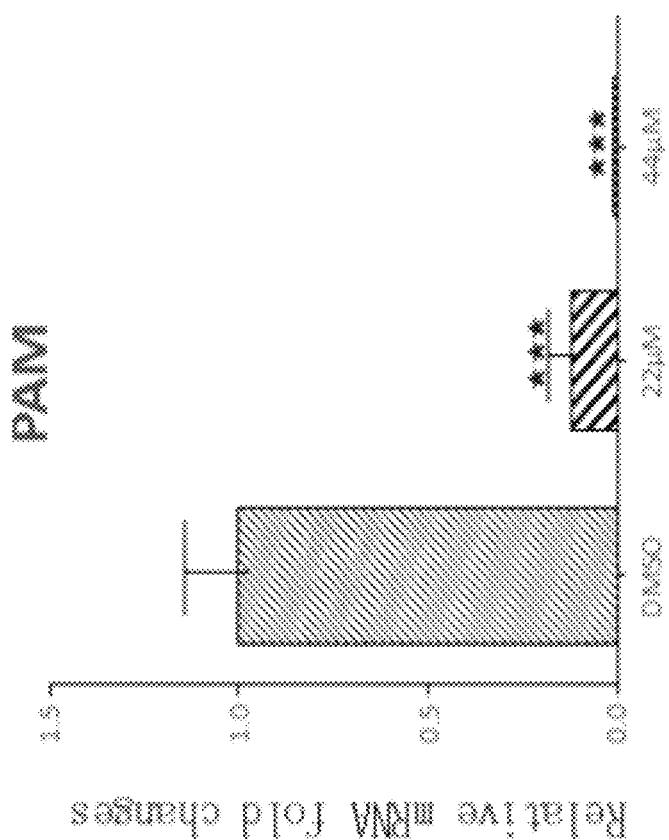
Figure 6:
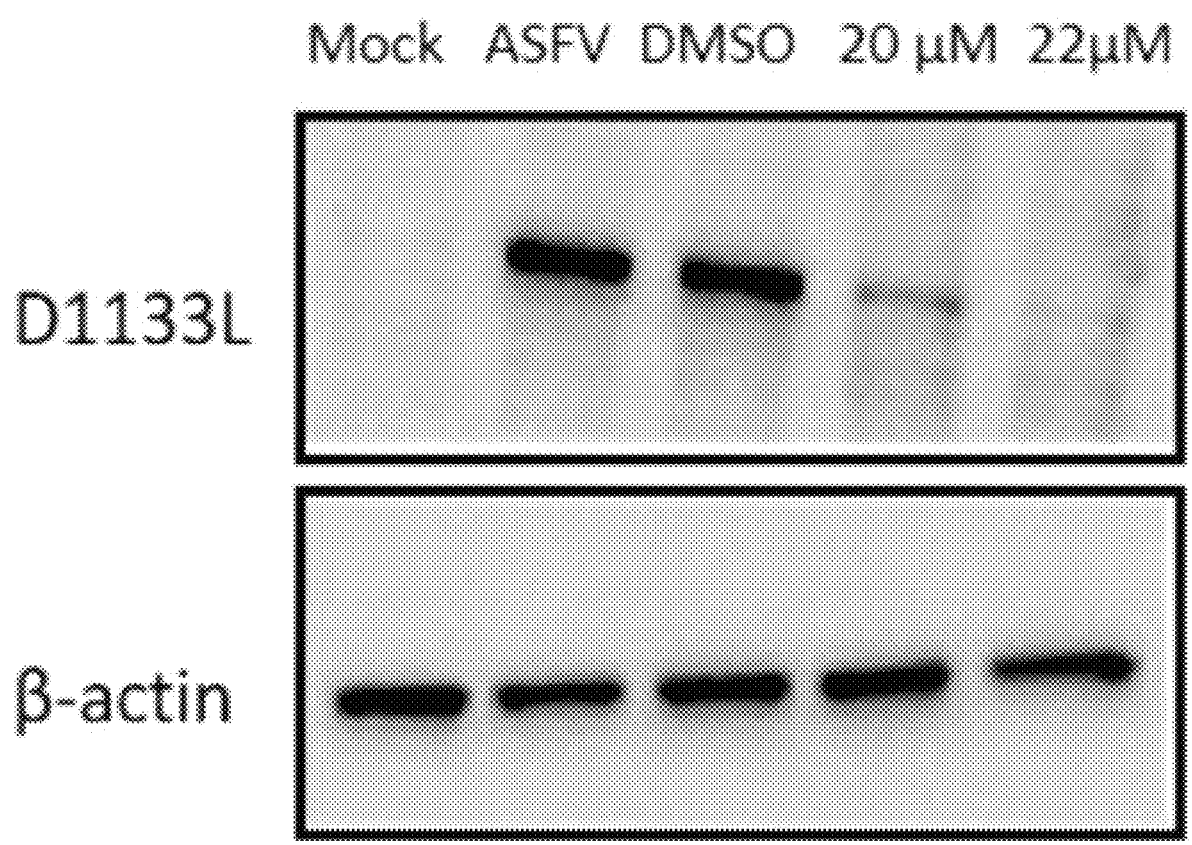
FIG. 6 shows that the compound aprepitant inhibits expression of a D1133L protein of the ASFV.
Figures 7A, 7B:
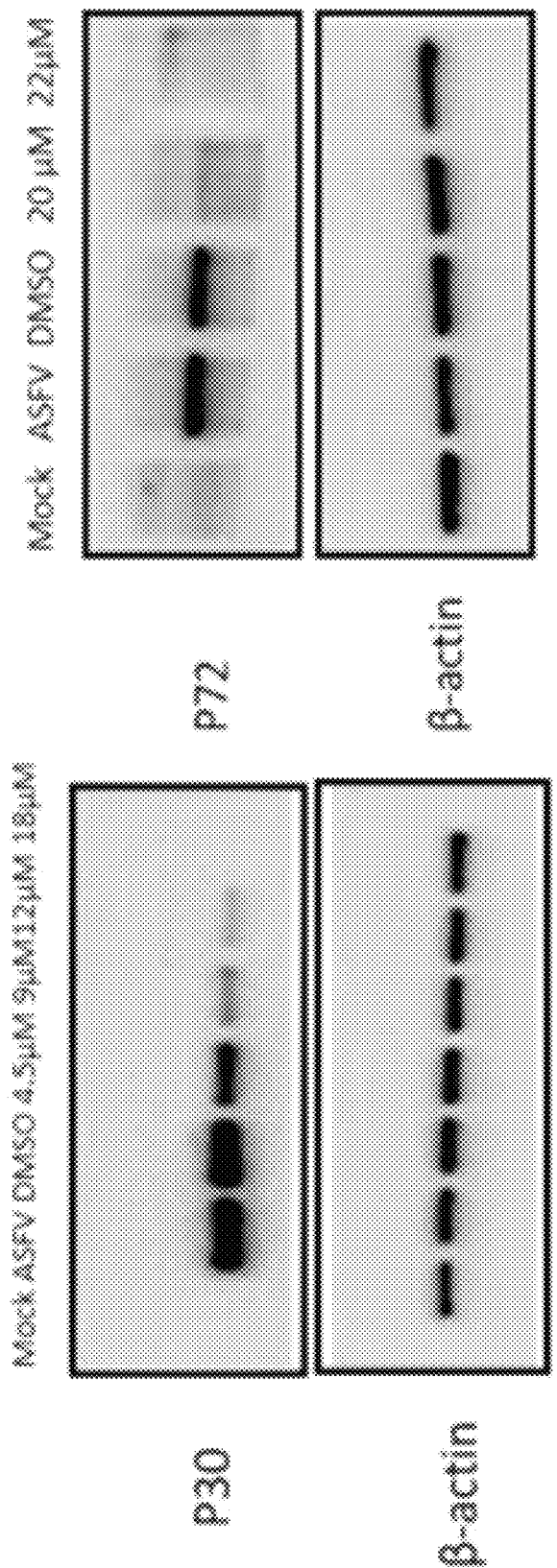
FIG. 7A-7B shows that the compound aprepitant inhibits expression of a p30 protein and a p72 protein of the ASFV; where

The results are shown in FIG. 4, the compound aprepitant can inhibit the RNA expression level of D1133L in the ASFV gene; when the compound aprepitant is dosed at 22 μM, the inhibition rate of D1133L RNA expression level is higher than 50%.

5. Effects of the compound aprepitant on RNA transcript levels of p30 and p72 of ASFV Porcine alveolar macrophages (PAM, $1\times10^6$/well) were cultured with an RPMI 1640+10% FBS medium in a 12-well plate, where in an experimental group, cells were treated with ASFV fluorescent virus (MOI=0.1) mixed with different concentrations of aprepitant (22 μM and 44 μM) dissolved in DMSO (<1%); in the infection control group, cells were treated with ASFV fluorescent virus (MOI=0.1) mixed with DMSO (<1%). The cell plate was cultured at 37° C. in 5% $CO_2$ for 48 h, and a cell culture was collected and centrifuged, and a supernatant was discarded. A total RNA was extracted by a TrizoL method, cDNA was synthesized by an RT Primer Mix kit, and the expression difference of the p30 and p72 RNA was detected by an RT-qPCR method.

An RT-qPCR reaction system had a total volume of 10 μL, including: 0.4 μL of each of upstream and downstream primers, 2 μL of the cDNA, 5 μL of TB Green™ Premix Ex Taq (TaKaRa), supplemented with sterile deionized water to 10 μL. The reaction was conducted by: at 95° C. for 2 min; at 95° C. for 10 sec; at 60° C. for 34 sec; conducting 40 cycles in total.

The primer sequences for amplifying p30 were: upstream primer: 5'-CTCCGATGAGGGCTCTTGCT-3' (SEQ ID NO: 6); downstream primer: 5'-AGACGGAATCCTCAG-CATCTTC-3' (SEQ ID NO: 7);

the primer sequences for amplifying p72 were: upstream primer: 5'-TGCGATGATGATTACCTT-3' (SEQ ID NO: 8); downstream primer: 5'-ATTCTCTTGCTCTGGATAC-3' (SEQ ID NO: 9).

The results are shown in FIG. 5, the compound aprepitant can inhibit the RNA expression levels of p30 and p72 in the ASFV gene; where the compound aprepitant inhibits the expression level of p30 RNA by more than 50% at a dosage of 22 μM, and inhibits the expression level of p30 RNA by more than 95% at a dosage of 44 μM; the compound aprepitant inhibits the expression level of p72 RNA by more than 50% at a dosage of 22 μM, and inhibits the expression level of p72 RNA by more than 95% at a dosage of 44 μM.

6. Effects of the compound aprepitant on an expression level of D1133L protein of ASFV Porcine alveolar macrophages (PAM, $1\times10^6$/well) were cultured with an RPMI 1640+10% FBS medium in a 12-well plate, where in an experimental group, cells were treated with ASFV fluorescent virus (MOI=0.1) mixed with different concentrations of aprepitant (20 μM and 22 μM) dissolved in DMSO (<1%); in the infection control group, cells were treated with ASFV fluorescent virus (MOI=0.1) mixed with DMSO (<1%). In addition, cells treated with only ASFV fluorescent virus (MOI=0.1) were used as an infection blank group. The cell plate was cultured at 37° C. in 5% $CO_2$ for 48 h, and a cell culture was collected and centrifuged, and a supernatant was discarded. A total protein was extracted, and the expression difference of D1133L protein was detected by Western blotting.

The result is shown in FIG. 6: compared with the uninfected control group (Mock group), the expression levels of D1133L protein in the infection blank group (ASFV), the infection control group (DMSO) and the experimental group (aprepitant +ASFV) each are increased; however, the expression level of D1133L protein is significantly decreased in the experimental group (aprepitant +ASFV) compared to the infection control group (DMSO). The results show that the compound aprepitant can significantly inhibit the expression level of D1133L protein in the ASFV gene.

7. Effects of the compound aprepitant on expression levels of p30 and p72 proteins of ASFV Pig alveolar macrophages (PAM, $1\times10^6$/well) were cultured in an RPMI 1640+10% FBS medium in a 12-well plate, where in the experimental group, the cells were treated with ASFV fluorescent virus (MOI=0.1) mixed with different concentrations of aprepitant (p30: 4.5 μM, 9 μM, 12 μM, 18 μM; p72: 20 μM, and 22 μM) dissolved in DMSO (<1%); and in the infection control group, the cells were treated with ASFV fluorescent virus (MOI=0.1) mixed with DMSO (<1%). In addition, cells treated with only ASFV fluorescent virus (MOI=0.1) were used as an infection blank group. The cell plate was cultured at 37° C. in 5% CO2 for 48 h, and a cell culture was collected and centrifuged, and a supernatant was discarded. A total protein was extracted, and the expression difference of p30 and p72 proteins was detected by Western blotting.

The result is shown in FIG. 7: compared with the uninfected control group (Mock group), the expression levels of p30 and p72 proteins in the infection blank group (ASFV), the infection control group (DMSO) and the experimental group (aprepitant+ASFV) each are increased; however, the expression level of p30 and p72 proteins is significantly decreased in the experimental group (aprepitant+ASFV) compared to the infection control group (DMSO). The results show that the compound aprepitant can significantly inhibit the expression level of p30 and p72 proteins in the ASFV gene.

The above results show that the compound aprepitant can significantly inhibit the RNA transcription and protein expression levels of ASFV, preventing virus invasion on host cells. Therefore, the compound aprepitant can be used to inhibit early and late infection of the ASFV.

EXAMPLE 2

Cytotoxicity of the Compound Aprepitant

Cytotoxicity assay was conducted on the small-molecule compound aprepitant by MTT assay on PAM cells. Porcine alveolar macrophages (PAMs, $2\times10^5$/well) were cultured in an RPMI 1640+10% FBS medium in a 96-well plate; different concentrations of aprepitant (20 μM, 40 μM, and 80 μM) dissolved in DMSO were added to the wells to treat the cells as an experimental group; meanwhile, a blank control group (medium+DMSO) and a negative control group (cells+medium+DMSO) were set up. The plate was incubated in an incubator for 48 h, and 10 μL of an MTT solution was added to each well of the plate; the plate was incubated in the incubator for 4 h, and 100 μL of a Formazan lysis solution was added to each well of the plate; the cells were mixed well, and continued to incubate in the cell incubator. The incubation was conducted until the Formazan was completely dissolved when observed under an ordinary light microscope. An absorbance at 570 nm measured by the microplate reader was read, and a cell viability of each concentration was calculated according to formula 1.

$$\text{Cell viability} = ((OD_{Dexperimental\ group} - OD_{blank\ control\ group})/(OD_{negative\ control\ group} - OD_{blank\ control\ group})) \times 100\%, \quad \text{Formula 1}$$

Figure 8:
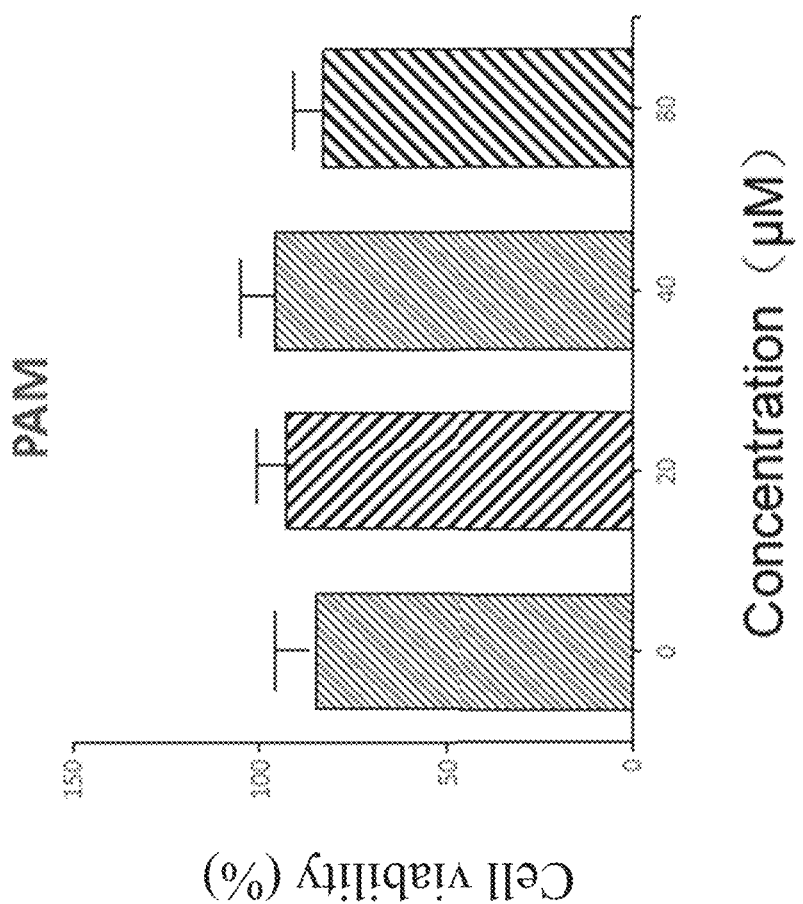
FIG. 8 shows a cytotoxicity test result of the compound aprepitant; where 0 refers to a negative control, while 20, 40, 80 refer to various concentrations of the aprepitant (20 μM, 40 μM, and 80 μM) dissolved in DMSO.

The results are shown in FIG. 8. The compound aprepitant has less toxicity to cells, and even when a dosage of the aprepitant reaches 80 μM, the cell viability can still reach more than 50%, indicating a low cytotoxicity and desirable safety.

In summary, the compound aprepitant of the present disclosure has a desirable inhibitory effect on ASFV, with a low cytotoxicity and desirable safety, which can be used for the prevention or treatment of ASF.

The above description of the examples is intended to help understand the method and core idea of the present disclosure. It should be noted that several improvements and modifications may be made by persons of ordinary skill in the art without departing from the principle of the present disclosure, and these improvements and modifications should also fall within the protection scope of the present disclosure. Various modifications to these examples are readily apparent to persons skilled in the art, and the generic principles defined herein may be practiced in other examples without departing from the spirit or scope of the present disclosure. Thus, the present disclosure is not limited to the examples shown herein but falls within the widest scope consistent with the principles and novel features disclosed herein.

What is claimed is:

1. A method for treating African swine fever (ASF), comprising administering a drug comprising a compound aprepitant to a subject in need thereof, wherein the compound aprepitant has a structural formula shown in formula (I):

Formula I

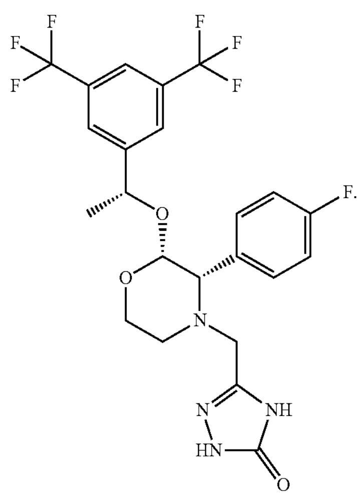 [SMILES: C[C@@H](O[C@H]1OCCN(Cc2n[nH]c(=O)[nH]2)[C@H]1c1ccc(F)cc1)c1cc(C(F)(F)F)cc(C(F)(F)F)c1]

2. The method according to claim 1, wherein the drug is a tablet, a spray, a granule, a capsule, an oral solution, an injection, or a suspension obtained by adding a pharmaceutically acceptable carrier and/or auxiliary material to the compound aprepitant.

3. The method according to claim 1, wherein the compound aprepitant has a treatment concentration of not less than 20 μM.

4. The method according to claim 3, wherein the compound aprepitant has a treatment concentration of 22 μM to 80 μM.

* * * * *

```
                        SEQUENCE LISTING

Sequence total quantity: 9
SEQ ID NO: 1            moltype = DNA  length = 20
FEATURE                 Location/Qualifiers
source                  1..20
                        mol_type = other DNA
                        note = upstream primer for ASFV-p72
                        organism = synthetic construct
SEQUENCE: 1
gataccacaa gatcagccgt                                                   20

SEQ ID NO: 2            moltype = DNA  length = 25
FEATURE                 Location/Qualifiers
source                  1..25
                        mol_type = other DNA
                        note = downstream primer for ASFV-p72
                        organism = synthetic construct
SEQUENCE: 2
ctgctcatgg tatcaatctt atcga                                             25

SEQ ID NO: 3            moltype = DNA  length = 25
FEATURE                 Location/Qualifiers
source                  1..25
                        mol_type = other DNA
                        note = ASFV probe primer
                        organism = synthetic construct
SEQUENCE: 3
ccacgggagg aataccaacc cagtg                                             25

SEQ ID NO: 4            moltype = DNA  length = 20
FEATURE                 Location/Qualifiers
source                  1..20
                        mol_type = other DNA
                        note = upstream primer sequences for amplifying D1133L
                        organism = synthetic construct
SEQUENCE: 4
cttctggaaa acggggtaca                                                   20

SEQ ID NO: 5            moltype = DNA  length = 20
FEATURE                 Location/Qualifiers
source                  1..20
                        mol_type = other DNA
                        note = downstream primer sequences for amplifying D1133L
                        organism = synthetic construct
SEQUENCE: 5
caagataaga accccgaca                                                    20

SEQ ID NO: 6            moltype = DNA  length = 20
FEATURE                 Location/Qualifiers
source                  1..20
                        mol_type = other DNA
                        note = upstream primer sequences for amplifying p30
                        organism = synthetic construct
SEQUENCE: 6
ctccgatgag ggctcttgct                                                   20

SEQ ID NO: 7            moltype = DNA  length = 22
FEATURE                 Location/Qualifiers
source                  1..22
```

-continued

```
                        mol_type = other DNA
                        note = downstream primer sequences for amplifying p30
                        organism = synthetic construct
SEQUENCE: 7
agacggaatc ctcagcatct tc                                      22

SEQ ID NO: 8            moltype = DNA  length = 18
FEATURE                 Location/Qualifiers
source                  1..18
                        mol_type = other DNA
                        note = upstream primer sequences for amplifying p72
                        organism = synthetic construct
SEQUENCE: 8
tgcgatgatg attacctt                                           18

SEQ ID NO: 9            moltype = DNA  length = 19
FEATURE                 Location/Qualifiers
source                  1..19
                        mol_type = other DNA
                        note = downstream primer sequences for amplifying p72
                        organism = synthetic construct
SEQUENCE: 9
attctcttgc tctggatac                                          19
```